United States Patent
Ulianov et al.

(10) Patent No.: US 11,494,963 B2
(45) Date of Patent: Nov. 8, 2022

(54) METHODS AND SYSTEMS FOR GENERATING A RESOLVED THREEDIMENSIONAL (R3D) AVATAR

(71) Applicant: Goodsize Inc., Wilmington, DE (US)

(72) Inventors: Dmitrii Ulianov, Moscow (RU); Igor Pasechnik, Moscow (RU); Ahmedkhan Shabanov, Dagestan (RU); Vadim Lebedev, Saint Petersburg (RU); Ilya Krotov, Kaliningrad (RU); Nikolai Chinaev, Moscow (RU); Bulat Yakupov, Tatarstan (RU); Vsevolod Poletaev, Moskovskaya obl (RU)

(73) Assignee: GOODSIZE INC., Wilmington, DE (US)

(*) Notice: Subject to any disclaimer, the term of this patent is extended or adjusted under 35 U.S.C. 154(b) by 25 days.

(21) Appl. No.: 17/093,146

(22) Filed: Nov. 9, 2020

(65) Prior Publication Data
US 2021/0150792 A1  May 20, 2021

Related U.S. Application Data

(60) Provisional application No. 62/936,197, filed on Nov. 15, 2019, provisional application No. 63/045,132, filed on Jun. 28, 2020.

(51) Int. Cl.
| | |
|---|---|
| *G06T 15/00* | (2011.01) |
| *G06T 13/40* | (2011.01) |
| *G06T 19/20* | (2011.01) |
| *G06T 7/50* | (2017.01) |
| *G06T 7/194* | (2017.01) |

(Continued)

(52) U.S. Cl.
CPC ............ *G06T 13/40* (2013.01); *A63F 13/537* (2014.09); *G06N 5/04* (2013.01); *G06N 20/00* (2019.01);

(Continued)

(58) Field of Classification Search
USPC .......................................... 345/418
See application file for complete search history.

(56) References Cited

U.S. PATENT DOCUMENTS 10,092,191 B2 * 10/2018 Yu ............................. G06T 11/00
11,210,838 B2 * 12/2021 Du ........................... G06T 15/04

(Continued)

OTHER PUBLICATIONS

Chen X, Pang A, Zhu Y, Li Y, Luo X, Zhang G, Wang P, Zhang Y, Li S, Yu J. Towards 3d human shape recovery under clothing. CoRR abs/1904.02601. Apr. 2019.*

(Continued)

*Primary Examiner* — Phu K Nguyen
(74) *Attorney, Agent, or Firm* — The Roy Gross Law Firm, LLC; Roy Gross

(57) ABSTRACT

Disclosed is a method and system for aligning separately created 3-D mesh of a body and head of a user for resolved 3-D avatar construction, comprising the steps of: estimating frame-to-frame pixel correspondences among selected frames for each of a separately captured body and head frame for creating a 3-D mesh for each of the body and the head; aligning the body 3-D mesh with the head 3-D mesh; and applying texturing to the aligned 3-D mesh by projecting the colors frames to the mesh posed in each frame pose and averaging the textures, thereby constructing a resolved 3-D avatar of the user.

21 Claims, 11 Drawing Sheets

(51) Int. Cl.
    *G06Q 30/06*     (2012.01)
    *G16H 40/67*     (2018.01)
    *G16H 50/50*     (2018.01)
    *G06Q 50/26*     (2012.01)
    *G06N 20/00*     (2019.01)
    *G06N 5/04*     (2006.01)
    *A63F 13/537*     (2014.01)
    *G06T 17/20*     (2006.01)

(52) U.S. Cl.
    CPC ....... *G06Q 30/0643* (2013.01); *G06Q 50/265* (2013.01); *G06T 7/194* (2017.01); *G06T 7/50* (2017.01); *G06T 17/20* (2013.01); *G06T 19/20* (2013.01); *G16H 40/67* (2018.01); *G16H 50/50* (2018.01); *G06T 2207/20081* (2013.01); *G06T 2207/30196* (2013.01); *G06T 2219/2004* (2013.01); *G06T 2219/2012* (2013.01)

(56) References Cited

U.S. PATENT DOCUMENTS

| | | | |
|---|---|---|---|
| 2016/0206203 A1* | 7/2016 | Yu | G06T 15/08 |
| 2019/0213778 A1* | 7/2019 | Du | G06T 17/00 |
| 2020/0066026 A1* | 2/2020 | Du | G06T 15/04 |
| 2021/0150792 A1* | 5/2021 | Ulyanov | A63F 13/537 |

OTHER PUBLICATIONS

Zanfir M, Popa Al, Zanfir A, Sminchisescu C. Human appearance transfer. InProceedings of the IEEE Conference on Computer Vision and Pattern Recognition 2018 (pp. 5391-5399).*

Tong J, Zhou J, Liu L, Pan Z, Yan H. Scanning 3d full human bodies using kinects. IEEE transactions on visualization and computer graphics. Mar. 9, 2012;18(4):643-50.*

* cited by examiner

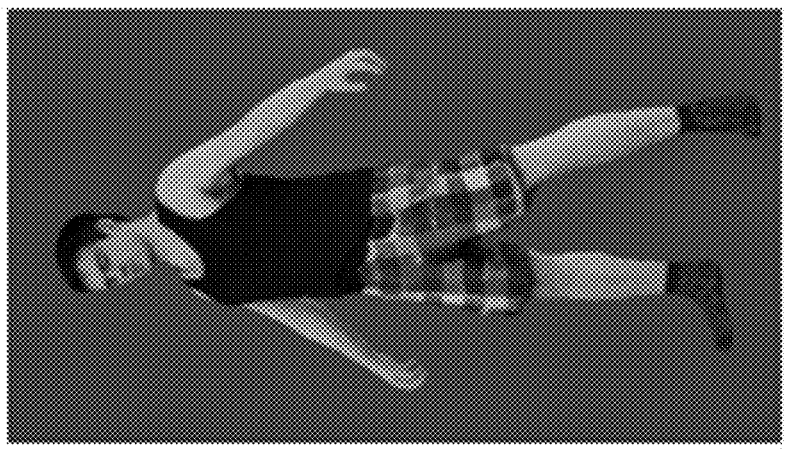
FIG. 8b Reconstructed avatar with texture
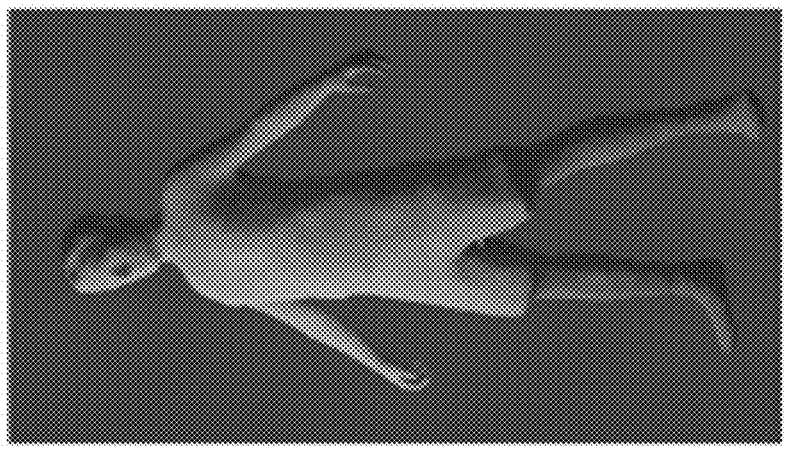
FIG. 8a Reconstructed avatar without texture

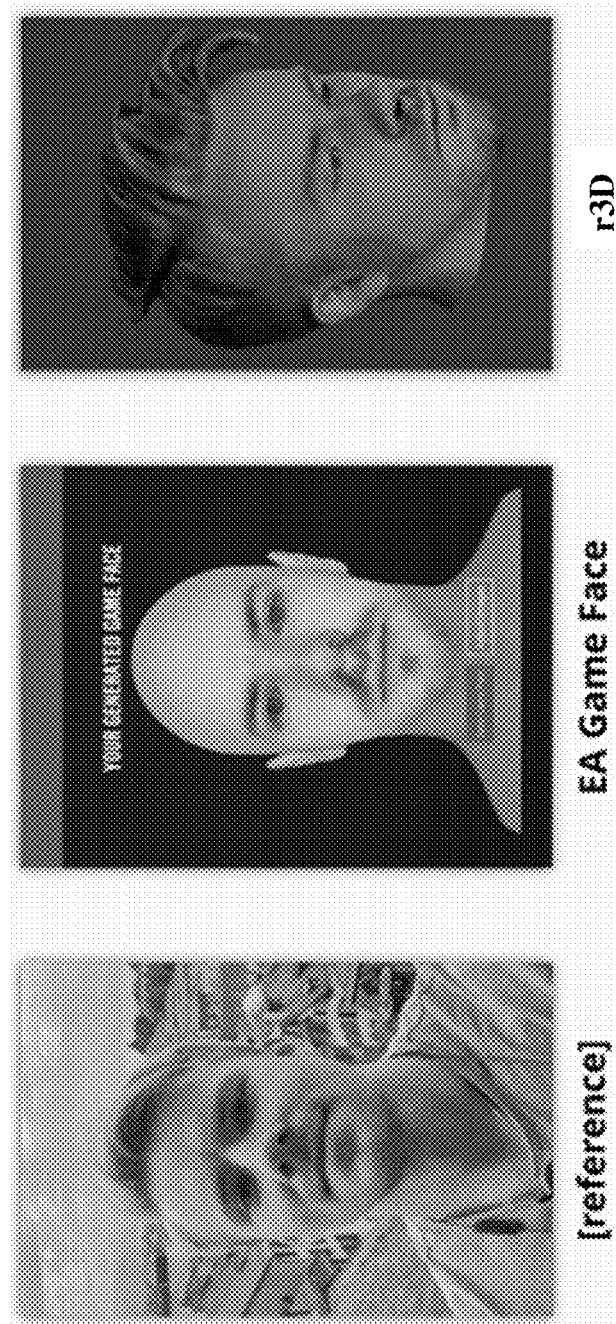
FIG. 9a [reference]
FIG. 9b EA Game Face
FIG. 9c r3D

METHODS AND SYSTEMS FOR GENERATING A RESOLVED THREEDIMENSIONAL (R3D) AVATAR

TECHNICAL FIELD

The present invention generally relates to the field of avatar generation, and in particular, the disclosure relates to methods and systems for generating a resolved three-dimensional (r3D) avatar.

BACKGROUND

With the ubiquity of mobile devices and image capture from said devices, there has been a dizzying array of mobile-based applications that incorporate a virtual representation or digital persona of the user-adding an immersive and representational value to the applications. As the next generation of consumers increasingly reside in the digital realm, the pervasiveness of and interactivity with digital personas is all but inevitable. The global apparel retail market is estimated to account for US$1.7 trillion (2018), of which online sales are expected to account for greater than 8%, providing a market opportunity exceeding US$136 billion with online sales growing at a steady 17% year on year. These estimates do not even account for all of the social restrictions due to the recent pandemic and the inevitable rise in shelter-in-place apparel shopping. As apparel retail shifts from brick-and-mortar to on-line, it is imperative for retailers to achieve more accurate garment fitting.

There are a number of existing applications that allow a user to generate a 3-D avatar of oneself for purposes of more accurate garment fitting, however, they appear low-definition—detracting from the virtual apparel fitting experience. The low definition inspires low confidence in the fitting, eventually resulting in the burden of dealing with a high rate of returns and lower sales for the apparel retailer. According to recent studies, over a third of all on-line apparel purchases result in a return. What's more, 78% of these returns are due to a fitting error. Moreover, other domains outside of apparel retail, such as apparel design and development, augmented reality/virtual reality, cosmetics, tele-medicine, video games, motion graphics, illustrations, film, virtual goods market, could all receive a boost from a higher resolution 3-D avatar to all links in their respective value chains.

Pipelines aided by trained networks to infer texturing and reflectances for generating photorealistic renderings are needed to fill this ever-gaping void in the digital realm. Increasingly resolved 3-D avatars are much needed to restore consumer and overall digital confidence during recent pandemic-related shifts in digital behavior. Moreover, extant systems do not continuously learn and update a deep neural network or discriminative library, which attempts to dynamically learn and predict finer facial, head, and figure nuances, in order to create shortcuts in the input processing. Such shortcuts may cut down on latency between image capture and avatar output, providing for a substantially more real-time experience. Moreover, such shortcuts may reduce the load bearing of the system and increase overall compute efficiencies. Extant 3-D avatar solutions lack the resolution that savvy netizens will soon demand—as they continue to forge into the deeper recesses of the digital realm—increasingly engaging in video conferencing; creating social media animations; fitting virtually for garments; consulting virtually a physician, etc.

SUMMARY

An embodiment of the invention discloses for a pipeline generating a resolved three-dimensional (r3D) avatar. A method for generating an r3D avatar comprises the step of: aligning separately created 3-D mesh topology of a body and head of a user for generating a resolved 3-D (r3D) avatar construction.

In another embodiment, r3D avatar construction comprises the steps of: estimating frame-to-frame pixel correspondences among selected frames for each of a separately captured body and head frame for creating a 3-D mesh for each of the body and the head; aligning the body 3-D mesh with the head 3-D mesh; and finally applying texturing to the aligned 3-D mesh by projecting the colors frames to the mesh posed in each frame pose (optionally, averaging the textures), and thereby constructing a resolved 3-D (r3D) avatar of the user.

In yet another embodiment of the r3D avatar construction, the method comprises the more detailed steps of selecting separately captured video frames of a human body and head of a user; performing depth-based segmentation to subtract background for each of the selected body and head frames; aligning a depth and color stream for each of the selected body and head frames; predicting correspondences between image pixels from each of the body and head frames and point on a surface of a parametric body model;
estimating frame-to-frame correspondences for creating a 3-D mesh for each of the body and the head; aligning the head 3-D mesh with the body 3-D mesh; and lastly, applying texturing to the 3-D mesh by projecting the colors frames to the mesh posed in each frame pose (optionally, averaging texturing) and thereby constructing a resolved three-dimensional (r3D) avatar of the user.

In yet other aspects, a system corresponding to the above disclosed r3D avatar generating pipeline is provided, replete with a r3D engine with distinct units and/or modules, such as a pre-processing module, processing module, and post-processing module. Generally, such units, modules, or engine are structurally in hardware, firmware, and/or software embodied using one or more processor, computer, controller, etc., to implement the afore-disclosed method steps for generating an r3D avatar.

BRIEF DESCRIPTION OF DRAWINGS

Other embodiments of this aspect include corresponding computer systems, apparatus, and computer programs recorded on one or more computer storage devices, each configured to perform the actions of the methods. These and other features and improvements of the present application will become apparent to one of ordinary skill in the art upon review of the following detailed description when taken in conjunction with the several drawings and the appended claims.

The drawings illustrate the design and utility of embodiments of the present invention, in which similar elements are referred to by common reference numerals. In order to better appreciate the advantages and objects of the embodiments of the present invention, reference should be made to the accompanying drawings that illustrate these embodiments.

Figure 1:
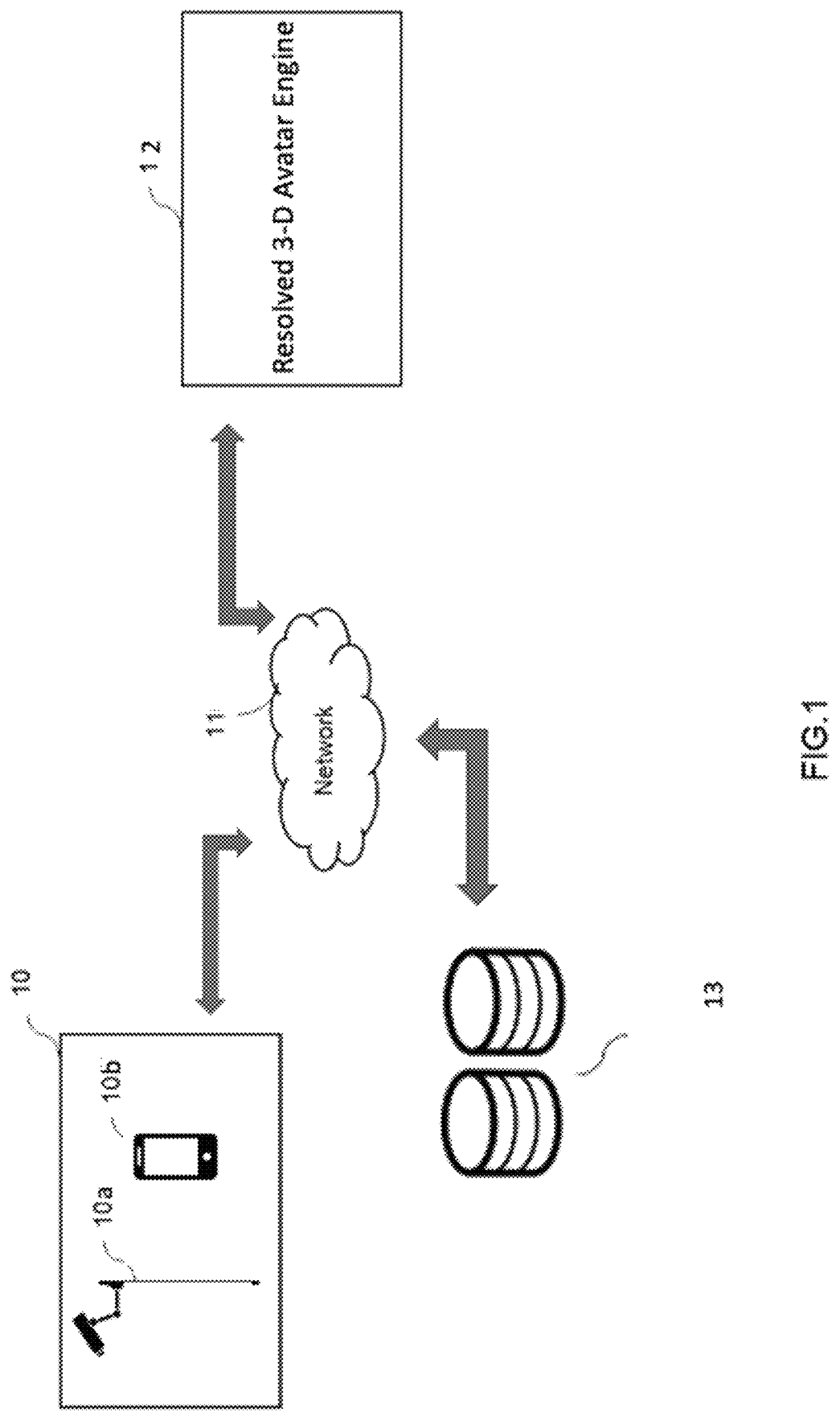

However, the drawings depict only some embodiments of the invention, and should not be taken as limiting its scope. With this caveat, embodiments of the invention will be described and explained with additional specificity and detail through the use of the accompanying drawings in which:

FIG. 1 illustrates an exemplary network environment in which various embodiments of the disclosure can be practiced.

Figure 2:
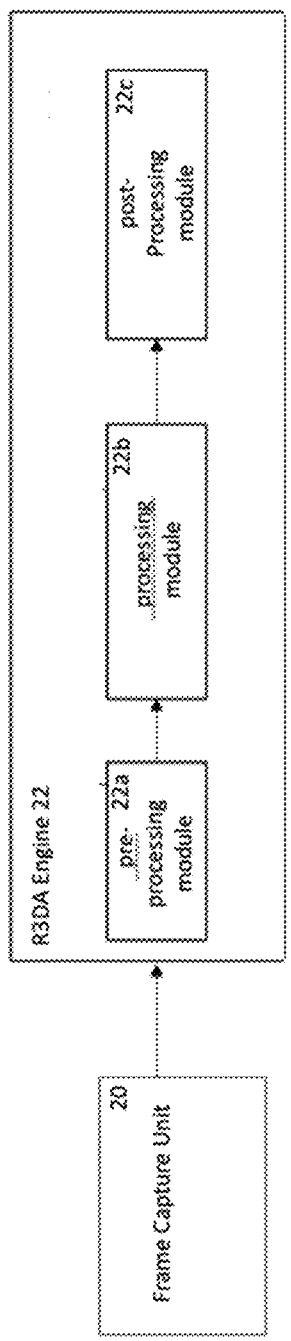

FIG. 2 illustrates a system diagram, according to an embodiment of the disclosure.

Figure 3:
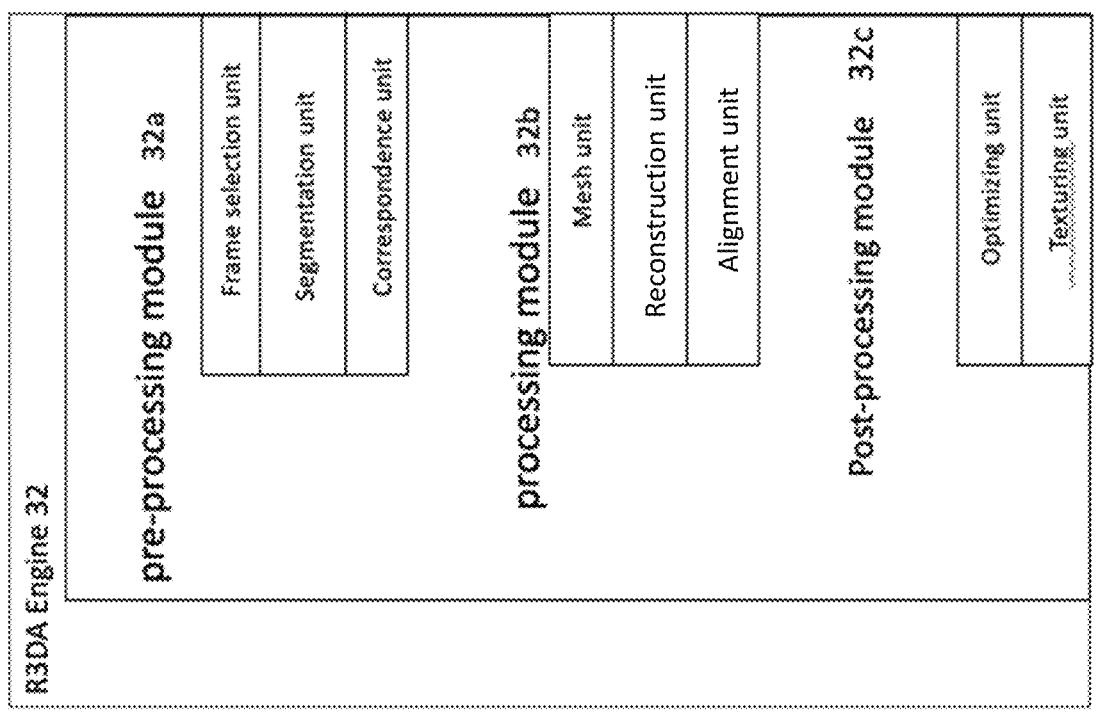

FIG. 3 illustrates a system diagram, according to an embodiment of the disclosure.

Figure 4:
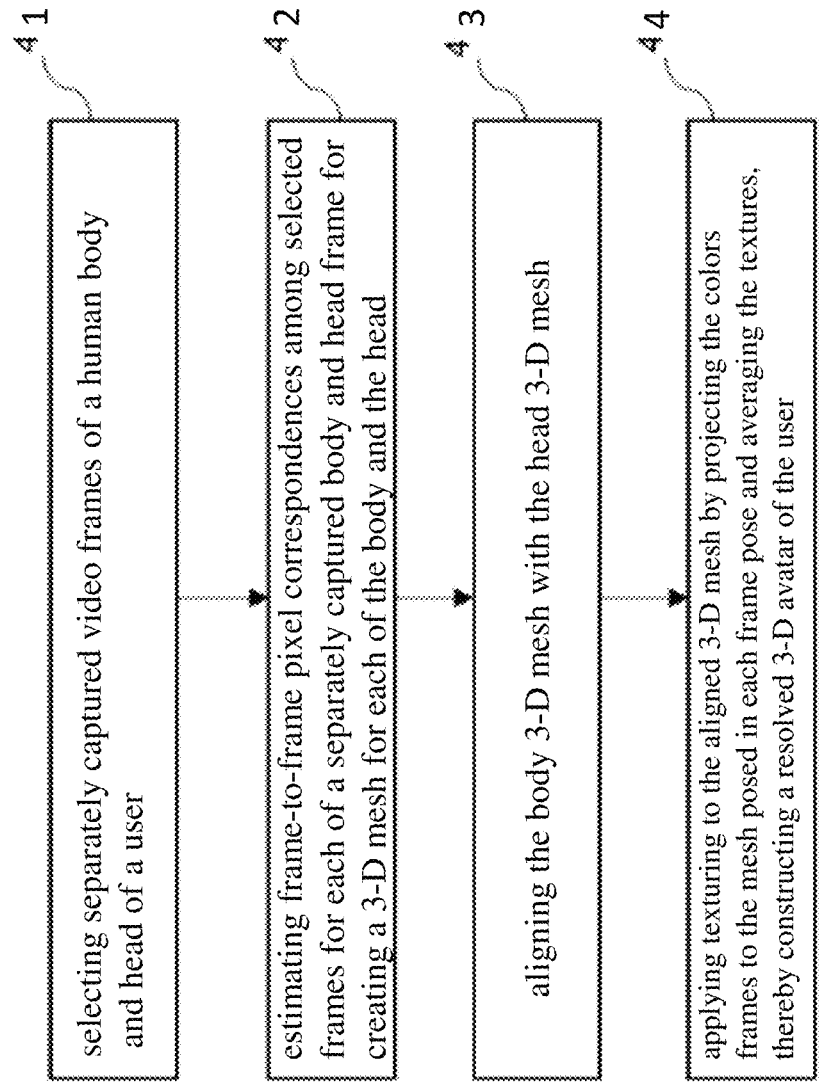

FIG. 4 is a method flowchart in accordance to an aspect of the invention.

Figures 5A, 5B:
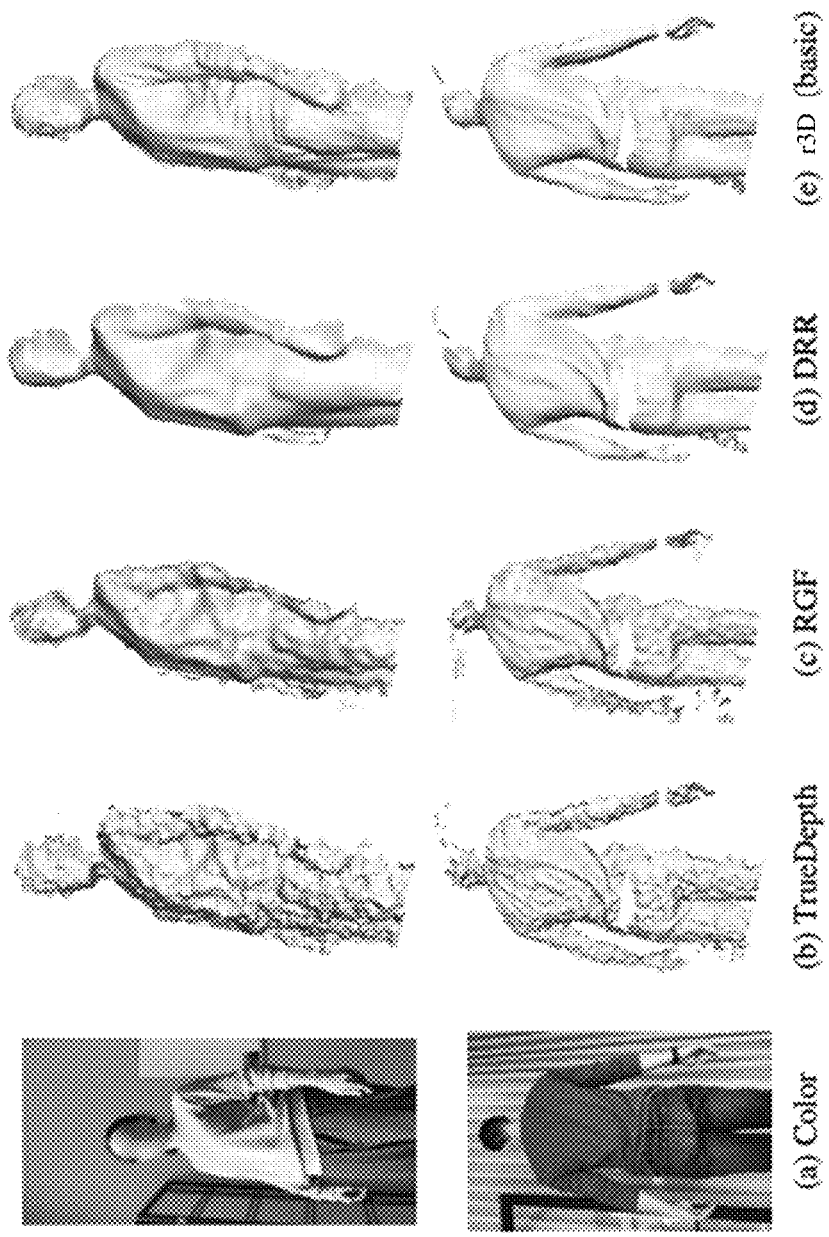

FIG. 5a is an avatar comparative in accordance with an aspect of the invention.

FIG. 5b is an avatar comparative in accordance with an aspect of the invention.

Figure 6:
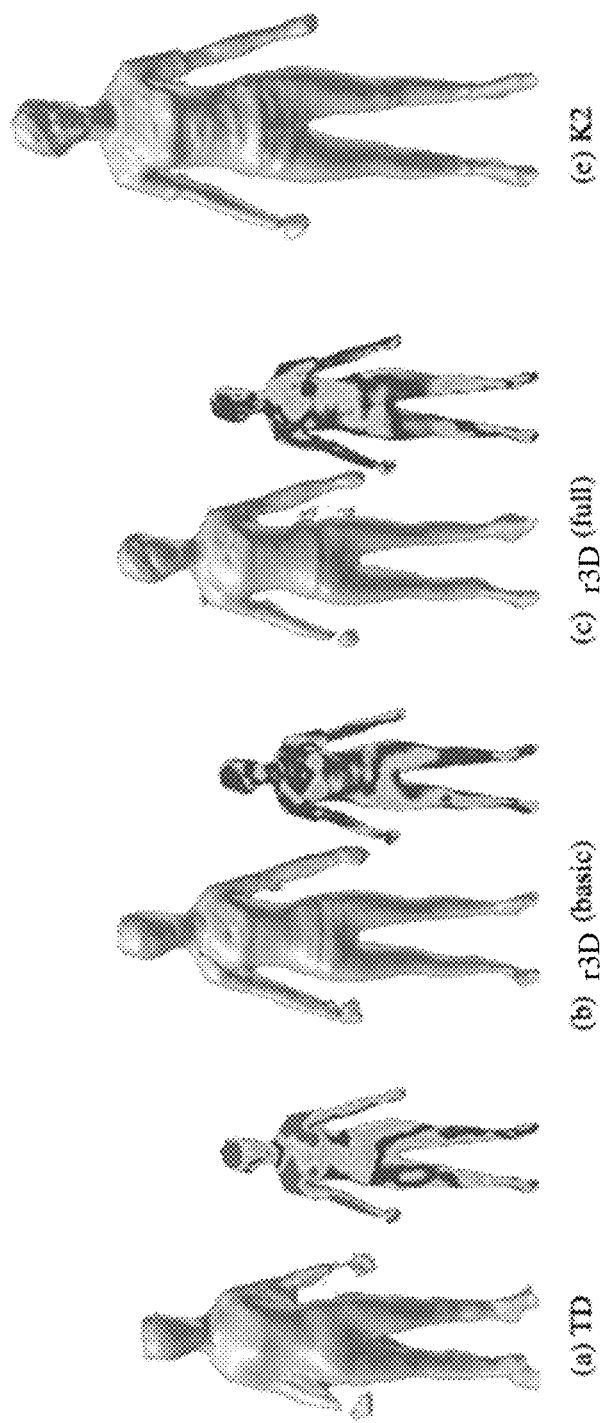

FIG. 6 is an avatar comparative in accordance with an aspect of the invention.

Figure 7A:
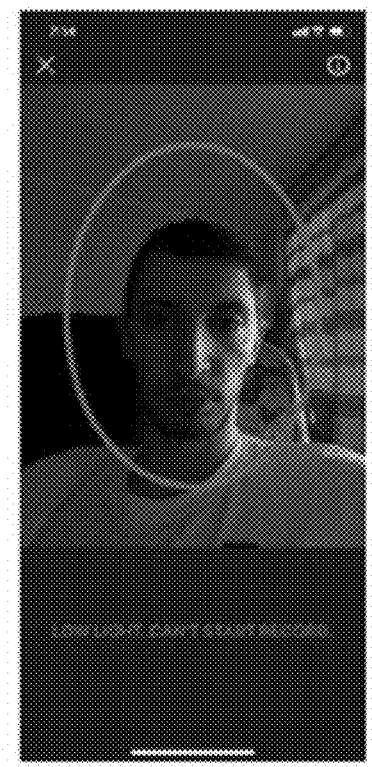

FIG. 7a is a screen shot of a user interface in accordance with an aspect of the invention.

Figure 7B:
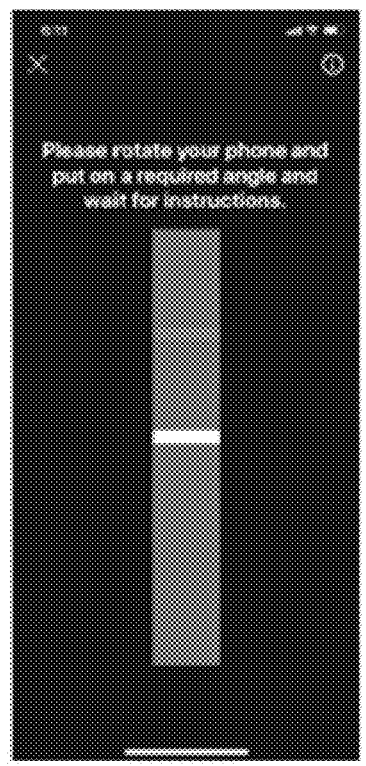

FIG. 7b is a screen shot of a user interface in accordance with an aspect of the invention.

FIG. 8a illustrates the impact of texturing in accordance with an aspect of the invention.

FIG. 8b illustrates the impact of texturing in accordance with an aspect of the invention.

FIG. 9a is an avatar comparative in accordance with an aspect of the invention.

FIG. 9b is an avatar comparative in accordance with an aspect of the invention.

FIG. 9c is an avatar comparative in accordance with an aspect of the invention.

Figures 10A, 10B:
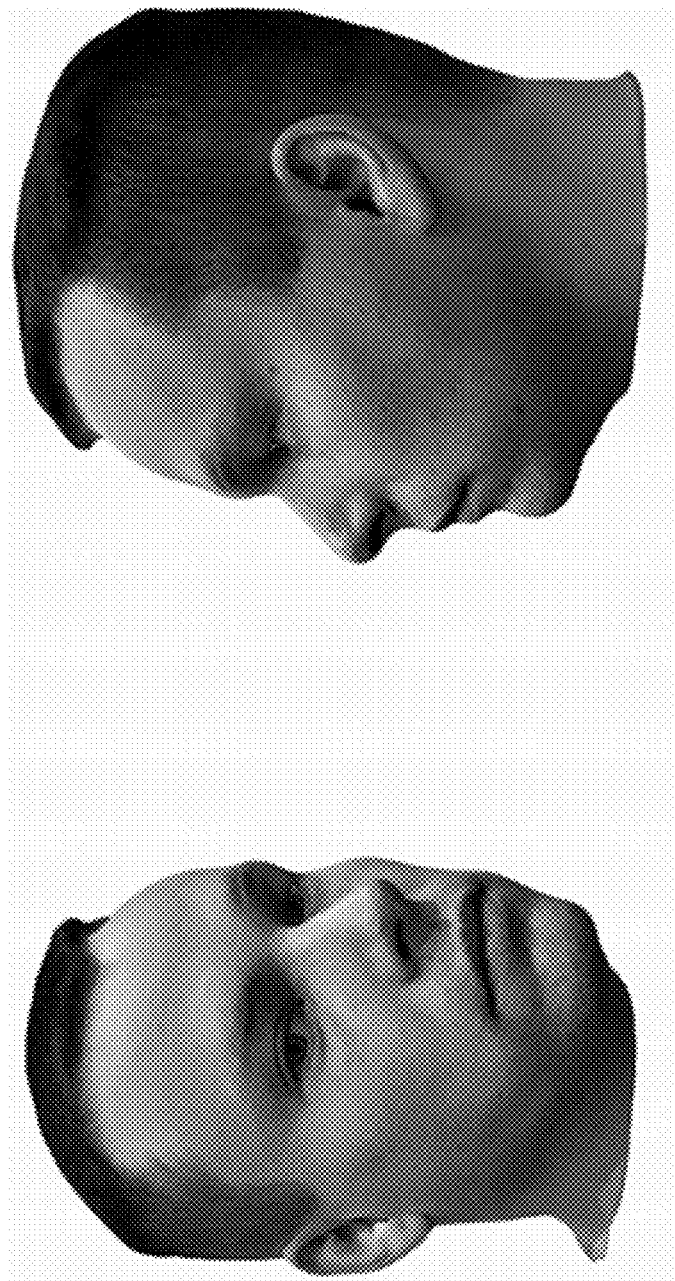

FIG. 10a is an example of a r3D avatar in accordance with an aspect of the invention.

FIG. 10b is an example of a r3D avatar in accordance with an aspect of the invention.

DETAILED DESCRIPTION OF DRAWINGS

The present invention will now be described more fully with reference to the accompanying drawings, in which embodiments of the invention are shown. However, this disclosure should not be construed as limited to the embodiments set forth herein. Rather, these embodiments are provided so that this disclosure will be thorough and complete, and will fully convey the scope of the disclosure to those skilled in the art. Like numbers refer to like elements throughout.

Overview

The primary purpose of the disclosure is to enable scanning a user's head and body separately with a conventional capturing means (mobile device camera/depth sensors) for generating a resolved 3-D (R/r 3D) avatar via a r3D avatar generating pipeline with compute efficiencies. The value proposition of the r3D avatar may apply to all links in the value chain for manufacturers, suppliers, and retailers for a number of different domains. The domain at focus initially is the apparel-fitting domain. The reason for this is due to the market potential for apparel retail, not to mention that apparel retail traditionally has had lower barriers to entry and has long been known to be early adopters.

Exemplary Environment

FIG. 1 illustrates an exemplary network environment in which various embodiments of the present invention can be practiced. The environment includes a r3D engine/module or R3D engine/module 12, in communication with a network, which in turn is in communication with server/cloud 13, fixed camera for frame/video capture 10a or mobile device camera for frame/video capture 10b. Optionally (not shown), the environment may also a real-time streaming system and video/image archive for surveillance/security applications, for instance. The frame/video capturing devices 10a/b include, but are not limited to, Closed-Circuit Television (CCTVs) cameras, High Definition (HD) cameras, non-HD cameras, handheld cameras, mounted cameras, device-embedded cameras (tablets, mobile devices, etc.) or any other video/image grabbing units. In one embodiment, the server 13 may receive a dynamic imagery, captured frame, or sequence of frames from a video footage from the frame/video capturing device 10a/10b and transmits the data to the r3D engine 12. Alternatively, the r3D engine 12 may be configured to receive an image/frame directly from capturing device. In other embodiments, the server 13, upon request, may retrieve archived images, frames, or footage for relaying to the r3D engine 12. The server is a data storage that is configured to store pre-recorded or archived videos/images. The server 13 may be composed of a plurality of local databases or remote databases. Also, the databases may be centralized and/or distributed. In an alternate scenario, the server 13 may store data using a cloud based scheme.

The network 11 may be any suitable wired network, wireless network, a combination of these or any other conventional network, without limiting the scope of the present invention. Few examples may include a LAN or wireless LAN connection, an Internet connection, a point-to-point connection, or other network connection and combinations thereof. The network 11 may be any other type of network that is capable of transmitting or receiving data to/from host computers, personal devices, telephones, video/image capturing devices, video/image servers, or any other electronic devices. Further, the network 11 is capable of transmitting/sending data between the mentioned devices. Additionally, the network 11 may be a local, regional, or global communication network, for example, an enterprise telecommunication network, the Internet, a global mobile communication network, or any combination of similar networks. The network 11 may be a combination of an enterprise network (or the Internet) and a cellular network, in which case, suitable systems and methods are employed to seamlessly communicate between the two networks. In such cases, a mobile switching gateway may be utilized to communicate with a computer network gateway to pass data between the two networks. The network 11 may include any software, hardware, or computer applications that can provide a medium to exchange signals or data in any of the formats known in the art, related art, or developed later.

Broadly, the r3D engine 12 or r3D avatar generating pipeline processes the one or more received images (or frames of videos) and executes a technique for aligning separately created 3-D mesh of a body and head of a user for resolved 3-D (r3D or R3D) avatar creation. The events in the pipeline are described in the following paragraphs, with reference to FIGS. 2-10b.

Recording Event:

A device with one or more cameras is placed or held either vertically or at an angle. A device can either have a depth camera or a regular RGB camera. A person positions the device and stands into a prompted pose/position for ideal frame capture. The prompts may be vocal and/or based on aligning a visual mark or box on the device screen. FIG. 7a and FIG. 7b illustrates a screen shot of a user interface displaying a mark alignment prompt for optimal frame capture. As shown in FIG. 7a, the user interface consists of a red oval surrounding the face of the captured user with the text warning of a low-light condition. FIG. 7b displays a vertical bar with a white tick representing the desired angle of the capturing device and the blue tick representing the current angle of the capturing device. Video recording may either start automatically upon a correct detected position of a user, or it can be initiated by the user. In the latter case, the user or another person initiates the video recording by either a voice command or gesture, or by pressing a button on the device (soft or hard). After that, the device can either start the recording of the video immediately or after some delay. The device can record data from either all of its cameras or only a part of them. The streams from the cameras can be either synchronized or not synchronized. The length of the video being recorded can be either fixed or unlimited.

The user is then prompted to record another video for better detalization of the head in the 3D model. For this: the user is prompted to adjust the distance/angle of the capturing device such that the face/head fits a designated mark for ideal alignment (shown in FIG. 7a/7b). The user is guided to rotate the head while the video from the devices' cameras is recorded. The user is either asked to rotate the head in a circular way or from the center to right, left, top, bottom in a pre-defined or not pre-defined order. The user is then optionally prompted to record another video for better detalization of the hands in the 3D model. The following process is performed for both right and left hands or only for one of them: the user is asked to adjust the angle/distance the capturing device such that an opened hand fits the designated mark for ideal alignment, much the same way for body and head scanning. The hand could be facing forward or backwards. Additionally, the hand could be laying on a flat surface or held in the air. The user is guided to flip the hand forward to backward or vice versa depending on the initial position. It is to be understood to a person of ordinary skill in the art that the recording event may comprise any sequence of body part scanning for downstream frame capture and r3D pipeline processing.

Frame Capture Event:

FIG. 2 illustrates a frame capture unit 20 in communication with various components of the r3D engine 22 in accordance with an aspect of the invention. The r3D engine 22 includes a pre-processor module/unit 22a, a processor unit 22b, and a post-processor unit 22c. In another embodiment, the frame capture unit 20 may be comprised as part of the r3D engine 22. Preferably, the frame capture unit 20 is configured to receive data from at least one of the real-time streaming system, the video/image server, or capturing device (mobile device camera). The data primarily comprises of at least one image/frame captured in real-time by the video/image capturing devices. In an embodiment of the invention, the data corresponds to at least one video/image/frame (v/i/f) previously stored in the video/image server or capturing device memory (stored photos/video).

The v/i/f received by the frame capture unit 20 may be in at least one of the following formats: PDF, PCD, PSD, EPS, JPEG, JPG, JIF, JFIF, TIF, TIFF GIF, BMP, PNG, MOV, OGG, WMV, FLV, MP4, MPEG, AVI, QT and ARF. Further, the v/i/f may be of any size, color, or length. The v/i/f may comprise a single, converged RGB stream or an RGB-D video consisting of two synchronized streams (one with color data (RGB stream) and one with depth data (depth stream)). In the former case, the depth stream is obtained using a machine learning model such as neural net-work trained for monocular depth estimation leading to RGB-D video consisting of two synchronized streams as in the latter case.

The following data can be supplied as input: intrinsic matrices of sensors (RGB and depth sensors). Alternatively, accelerometer data can be optionally supplied. The RGB-D video is expected to have a user moving around. The movements can include, but not limited to, walking, turning around, moving hands, etc. A user is expected to move in such a way that maximal exposure of the scanned user portion is captured, along with maximal pose diversity of the scanned user portion. The frame capture unit 20 sends the received data (v/i/f) to the r3D engine 22, and more particularly, to the pre-processing module 22a of the r3D engine 20 for upstream pipeline processing.

Pre-Processing Event:

FIG. 3 illustrates a system diagram, according to an embodiment of the disclosure. More particularly, FIG. 3 expresses each of the pre-processing 32a, processing 32b, and post-processing 32c modules comprising the r3D engine 32. As shown in FIG. 3, specifically focused on the pre-processing module 32a, this module 32a further comprises a frame selection unit, a segmentation unit, and a correspondence unit.

Frame Selection Unit:

In an embodiment of the invention, the data received by the frame selection unit includes a video, i.e., a sequence of frames, or frames directly. In this case, "undesired" frames (user outside frame, lack of sharpness, another user appearing in frame, user within frame, but too close or far from capturing device, etc.) are removed prior to relaying to the frame selection unit. Additionally, a neural network may be used that is trained for key-point detection for body joints estimation. The network estimates up to 128 key-points and joints on the body, face and hands. In one embodiment, the removal of the "undesired" frames and the key-point detection of body joint estimation may be performed prior to relay to the frame selection unit. Alternatively, the frame selection unit may perform the aforementioned two steps prior to additional frame selection as part of the pre-processing event in the r3D pipeline.

The frame selection unit may perform sub-selection, wherein the selection method can be based on a user's poses detected at each frame to maximize their diversity (e.g. by using clustering of the poses from each frame) and total visible area (exposure area) of the users body surface while limiting the total amount of frames used. Alternatively, a simple uniform frame selection method can be used, wherein the frames are selected to be uniformly spaced one from the other. Once the sub-selection is done, the selected frames are relayed to the segmentation unit within the pre-processing module, which is configured to segment the user from the background.

Segmentation Unit

The following techniques may be performed to achieve segmentation:

Deep Neural Network-based model trained for user segmentation or segmentation of apparel.

Depth-based segmentation may be used to compute the maximum depth value $d_m$ over the sequence for each pixel. For a particular frame and particular pixel, the value d to the computed maximum value may be compared and assign a pixel background value, if d and $d_m$ are similar enough.

Background subtraction entails subtracting using a special "background frame" (a frame where only background is visible and the user is out of frame).

Prior to relaying the segmented frames to the correspondence unit for frame-to-frame correspondence, a fixing of color and stream alignment; an estimating of frame-to-parametric model surfaces; and an assignment of body parts to pixels may occur in the pre-processing pipeline.

Correspondence Unit:

Once again, a deep neural network may be trained to extract sparse or dense (optical flow) correspondences on RGB(D) images. This step provides correspondences between the pixels in the consecutive frames. Optionally, one may use separate extractors for different parts of the body (e.g. one model for head and another model for body). One may then leverage frame-to-parametric model to filter the frame-to-frame correspondences based on the distance between them on the parametric model surface. To generate the training data, in order to train a model on the data with known or estimated correspondences, one may use either synthetic data (e.g. animated 3-D models of humans rendered to images) or static objects scanned using (e.g. photogrammetry and rendered to images from different views) or the RGB(D) photos annotated by humans (e.g. a human set correspondences between the images). The filtered model is then sent to the processing module 32b for constructing the 3-D mesh topology of the head and body separately—in line to generate the r3D avatar.

Processing Event:

Mesh Unit:

The mesh unit, as part of the processing module 32b, is configured to receive the filtered frames for generating the 3-D mesh topology—a low-resolution parametric 3D mesh of the human body, accurately placed to match the user in every selected frame. It does this by first, body tracking, which entails (1) using custom parametric body model, parameterized by pose parameters P (and $\{$ optionall$\}$, shape parameters S, displacements for each vertex D); (2) treating the pose parameters as independent variables for every frame $P=P_1, \ldots, P_N$, and the shape and displacement parameters are shared among frames (the pose on each frame consists of components responsible for translation, global rotation, rotations of individual joints or bones. The location of vertices of the para-metric model at frame i is a function of $\{P_i, S, D\}$); applying an iterative optimization algorithm (such as LBFGS or Adam) is then used to find the parameters and based on the weighted sum of these losses: for each frame the parametric model's silhouette should coincide with the silhouette extracted from the RGB-D frame. To create a differentiable loss, once may apply distance transform to the segmentation mask of the user (created during the pre-processing step) and minimize its average value over the border of the rasterized 3D body for each frame.

In an embodiment of the invention, depth to parametric model depth error by calculating an average per-pixel error between the depth maps from the depth stream and parametric models' depth rendered to the camera. Optionally, one may use image pyramids for better gradient flow. Furthermore, one may calculate loss between point clouds in 3D by searching for the for the closest vertex in the corresponding 3D model. The loss value is an average distance between the matched points. Optionally, one may also use the information about the body parts predicted at stage 7 of the pre-processing pipeline in this loss. In this case, for each point e in the point cloud, one may search for the closest point only across the mesh vertices corresponding to the body part assigned to the point e. This enables much faster convergence.

In an embodiment of the invention, frame-to-parametric model surface correspondence error is calculated by using (X, Y, Z) or (U, V) or similar coordinates estimated at the pre-processing stage. Losses are created in several different ways: (1) projecting the current parametric model (one per frame) frame) to the camera. Thus, for each pixel, the (X, Y, Z) or (U, V) location of the parametric scan may be known. One may match this with the information obtained at the pre-processing stage. Additionally, one may compute the mean difference between the two and use it as the loss. Alternatively, if (X, Y, Z) are used: one may project the points corresponding to parametric model to the camera plane and do the same with the predicted (X, Y, Z). The discrepancy may be computed better for those two and use the average value of it as the loss.

In a preferred embodiment, one may use the correspondences between the frames extracted at the pre-processing stage. For any pair of corresponding points (one from frame i, one from frame j), one may project them to the corresponding meshes (mesh i and mesh j) and obtain $(x_1, y_1, z_1)$ and $(x_2, y_2, z_2)$ coordinates in 3D space. In one embodiment, one may transform those to a canonical space (with fixed pose) and compute the distance between those. The loss is an average distance between the corresponding points in canonical space over all the pairs of matches. Alternatively, similar to the Frame-to-parametric case, one may compute the distances between the 2D projections to camera instead of the points in 3D space.

Preferably, one may project the color frames to the surface of the parametric model, resulting in partial texture for each frame. One then may minimize the discrepancy between them by searching for the correspondences in the small area of each pixel. Optionally, one may also possibly optimize for the lighting.

For arm regularization loss, one may preferably force the angle of the bones with respect to the parent bones associated with left and right arm to be as similar as possible. One may use this loss if the movements are restricted to a turn-around. For displacement regularization loss, for each vertex, one may preferably force its displacement to be as close as possible to the average of the displacements of neighboring vertices.

Another term forces the displacements to have as low magnitude as possible (e.g. minimizes average L2 norm of displacements). In the interest of temporal consistency, this term works on the triplets of consecutive frames i, i+1, i+2. We force the average of parameters $P_i$ and $P_{i+2}$ to be as close as possible to the $\{\ \}$ parameters $P_{i+1}$ of the frame i+1. All losses are summed up with some weights and the gradients with respect to parameters P, S, D are calculated. Although here, the parametric 3D model was optimized, the same losses can be applied for optimization of non-parametric 3D model. In case one wants to optimize only displacements $D_n$ for the non-parametric 3D model, one can do it directly. Alternatively, one can also associate a parametric model with the non-parametric in canonic space and use any reposing or motion transfer method to transfer motions from the parametric models associated with each frame to the non-parametric model. Then, the reposed non-parametric models take part in loss calculation. In this case, one may optimize for $\{P, S, D, D_n\}$ or its subset.

Body Reconstruction Unit:

To reconstruct a body model, one may fit a low-detailed parametric model to each selected frame by the reconstruction unit. In an embodiment, the reconstruction unit estimates a well-detailed non-parametric surface of arbitrary topology. Each point cloud is transformed into a 3-D array of the values of projective signed distance function (PSDF), then these arrays are transformed to the pose of the first frame (canonical pose) using linear blend skinning or any other reposing method. In an embodiment, the reconstruction unit accumulates all of the PSDFs in a single truncated distance function (TSDF) cube. One may extract the mesh from the TSDF cube using marching cubes algorithm. Applying a Poisson surface reconstruction algorithm in order to render a watertight mesh.

Head Scan Reconstruction Unit:

Given an input RGB-D video, one may obtain the head scan following these Steps performed by the Reconstruction Unit, or optionally, by the Head Reconstruction Unit: pre-processing video by removing background; detecting 2d facial landmarks in the frames where a significant portion of the face is visible; estimating 6 DoF pose of the head in some of the frames by using depth information to back-project the 2d landmarks into 3d; computing a Procrustes alignment between consecutive frames; selecting a predefined but arbitrary amount of frames by running K-means clustering on the rotational components of the 6 DoF poses for the frames where pose information has been computed; sampling uniformly from the remaining frames; reordering the frames to ensure a substantial overlap between the head surface visible in every given frame and the head surface covered in the preceding frames; initializing a TSDF volume with predefined, but arbitrary, spatial resolution using head dimensions extracted from the first frame; and extracting PSDF from the first frame and integrate it into the volume. For every frame with a 6 DoF pose estimate available, extract the surface from the TSDF volume using marching cubes algorithm, using the estimated 6 DoF pose to initialize ICP, align the reconstructed surface with the frame point cloud using ICP algorithm; extract PSDF from the frame and integrate it into the volume. For every frame with 6 DoF pose estimate unavailable, copy the 6 DoF pose information from the neighboring frame and follow the previous steps. Reconstructing the head scan by running marching cubes on the estimated TSDF. Projecting the 2d facial landmarks from the first frame onto the head scan, store them as points in 3d. Finally, using the losses from section to further optimize the geometry of the face. The same overall reconstruction method may be performed by the reconstruction unit to reconstruct/refine the hand, or optionally, hand reconstruction/refinement may be performed by a dedicated hand reconstruction/refinement unit.

Alignment Unit:

The alignment unit estimates the 6 DoF pose of the head scan relative to the body model. In an embodiment, one may use the following 2D and 3D cues in order to accomplish that:

ICP between the head scan and the head of the underlying parametric model.

ICP between the head scan and the head of the reconstructed body model.

ICP between the head scan and the first depth frame of the body video.

2-D landmarks alignment between projected head scan landmarks and facial landmarks and facial landmarks of the first RGB frame of the body video. Silhouette of the head scan in the first frame of the body video. The losses are summed with weights and optimized using LBFGS or an Adam optimizer.

Furthermore, the alignment unit may deform the head part of the body model into the shape of the head scan in the following steps:

Locate the head polygons of the body model by finding the closest head scan vertex for each body vertex, computing distances and thresholding these distances.

Subdivide the head polygons of the body model by splitting the edges at midpoints.

Estimate displacements for the body vertices by computing a point-to-plane ICP loss between the body vertices and the head scan vertices and using a Laplacian smoothness term as a regularizer.

Post-Processing Event:

Optimizing Unit/Texturing Unit:

Having a reconstructed mesh, the optimizing unit may optionally re-mesh it to simplify topology and smooth it. Optionally, the optimizing unit may optimize the displacements of the resulting mesh further using the losses from the section. The r3D engine/pipeline then texturize the mesh by projecting the color frames to the mesh posed in each frame's pose and averaging the textures by the texturizing unit. Alternatively, texturizing may be performed by simply projecting the color frames to the mesh posed in each frame's pose without averaging the textures. The final optimization and texturing results in the resolved 3-D (r3D) avatars (see FIG. 8b illustrating a r3D avatar using the r3D pipeline in comparison with a non-r3D avatar as shown in FIG. 8a; and FIGS. 10a/10b, which both illustrate r3D avatars using the r3D pipeline in varying head perspectives). Alternatively, while potentially rendering less smooth or resolved r3D avatars, the r3D engine or pipeline may exclude the steps of predicting correspondences between image pixels from each of the body and head frames and point on a surface of a parametric body model; and estimating frame-to-frame correspondences for creating a 3-D mesh for each of the body and the head. Furthermore, a potential shortcut to the pipeline may be: 1) using the aforementioned methods to create a dataset, the dataset may consist of pairs [RGB(D)] images, parameters of 3D avatar in the pose of the person on the image such that the avatar projects to the person on the image; 2) training a neural network to predict the parameters of the 3D avatar that would normally result by running optimization; and 3] predicting parameters for each frame and fine-tuning them with optimization techniques/results as described above.

FIG. 4 illustrates an exemplary method flow of the r3D engine/pipeline. In a preferred embodiment, as shown, the method for aligning separately created 3-D mesh of a body and head of a user for resolved 3-D avatar construction, comprises the steps of: (1) selecting separately captured video frames of a human body and head of a user; (2) estimating frame-to-frame pixel correspondences among selected frames for each of a separately captured body and head frame for creating a 3-D mesh for each of the body and the head 42; (3) aligning the body 3-D mesh with the head 3-D mesh 43; and (4) applying texturing to the aligned 3-D mesh by projecting the colors frames to the mesh posed in each frame pose and averaging the textures, thereby constructing a resolved 3-D avatar of the user 43.

While not shown in FIG. 4, the method for constructing the r3D avatar may comprise selecting separately captured video frames of a human body and head of a user; performing depth-based segmentation to subtract background for each of the selected body and head frames; aligning a depth and color stream for each of the selected body and head frames; predicting correspondences between image pixels from each of the body and head frames and point on a surface of a parametric body model; estimating frame-to-frame correspondences for creating a 3-D mesh for each of the body and the head; aligning the head 3-D mesh with the body 3-D mesh; and applying texturing to the 3-D mesh by projecting the colors frames to the mesh posed in each frame pose, thereby constructing a three-dimensional avatar of the user.

While the end-use applications for the r3D avatar is endless given the value of incorporating a higher resolution digital persona of a user, some of the pertinent applications are as follows:
1. incorporated into an on-site and/or on-line apparel fitting/retail experience, wherein the experience includes providing precise body dimensions and/or virtual apparel fitting for purchase.
2. incorporated into an on-site and/or on-line Augmented Reality/Virtual Reality (AR/VR) experience.
3. incorporated into an on-site and/or on-line gaming experience.
4. incorporated into an on-site and/or on-line tele-medical application.
5. incorporated into an on-site and/or on-line dermatological or cosmetic purpose.
6. incorporated for surveillance, security, identification, or verification purposes, wherein the captured frames are from a remote stationary camera and/or database.

The initial deployment of the r3D avatar and engine/pipeline is configured for the first above listed application: r3D avatars with precise body dimensions for apparel/garment fitting/retail. In a preferred embodiment, the video scan provides the raw data which is needed for the processing part of the apparel fitting system. The video scan obtained through an SDK embedded within the online-retailer/3rd party app/website or the user scan interdependently through a native app. Thereafter, the data goes to processing in order to convert and extract the body data of the user, which may then can be streamed back to the buyer/retailer/3rd party through the API or SDK for insights and recommendation on apparel fitting for the user based on his/her body-data.

SDK for Mobile Devices:
record the video from all the cameras needed.
prepare the data for processing. This includes preparing all the data according to a required format and naming.
process the video (if processing is done on device).
interact with the cloud (i.e. upload the data for processing or upload the processing result, receive the processed result, receive status, list of available 3D avatars, etc.).

API:
access the 3D scan and download at as .obj or .glb file.
access the body measurements of the 3D scan and download them as .csv, .json or similar.
retrieve the recommendation system result.

In a preferred embodiment, the apparel fitting system returns the best appropriate clothing size (e.g., L or M) for a particular body, and optionally, brand/clothing id, e.g., identified by a link to a web site, based on the generated r3D avatar from the r3D engine/pipeline. The apparel fitting system is trained on a dataset of bodies with known best clothing size for a particular brand and possibly for a particular item. To train the system, up to 200 or so body measurements extracted from the 3-D body, such as waist circumference, etc., and a machine learning algorithm, such as random forest regressor or a neural network, is trained to predict the right size.

In instances where the capturing device is only disposed with a low-quality camera/depth sensor, a technique for denoising to render higher quality images for feeding into the r3D pipeline is also provided. In a preferred embodiment, the pipeline for generating a r3D avatar from a low-quality capturing device may further comprise the step of: referencing a training dataset to predict a high quality (HQ) depth sensor image frame reprojection from a capturing view of a low quality (LQ) depth sensor. With the more robust training set, higher quality images may be predicted using the various neural network/machine learning models in order to be fed into the r3D pipeline. This extension of the pipeline allows for r3D avatars being generated even with the low quality cameras/sensors disposed in typical user devices, such as a mobile device or tablet.

In a preferred embodiment, the denoising technique entails using non-synchronized streams coming from a pair of consumer-level depth sensors. By recording simultaneous depth sequences with a pair of lower-quality and a higher-quality RGB-D cameras, one may carefully align them both temporally and spatially and learn a deep neural network to denoise the lower-quality data using the higher-quality sensor as a source of supervision signal (reprojection, as described above). Notably, one may then use the same dataset to up-sample and refine higher-quality depth.

FIGS. 5a, 5b, 6, 9a, 9b, and 9c all illustrate a comparative between a r3D avatar (optionally, incorporating the added denoising extension) against 3-D avatars not generated by the r3D engine/pipeline (non-r3D avatars).

In the drawings and specification, there have been disclosed exemplary embodiments of the disclosure. Although specific terms are employed, they are used in a generic and descriptive sense only and not for purposes of limitation, the scope of the invention being defined by the following claims. Those skilled in the art will recognize that the present invention admits of a number of modifications, within the spirit and scope of the inventive concepts, and that it may be applied in numerous applications, only some of which have been described herein. It is intended by the following claims to claim all such modifications and variations which fall within the true scope of the invention.

Embodiments described in the present disclosure can be implemented by any system having a processor and a non-transitory storage element coupled to the processor, with encoded instructions stored in the non-transitory storage element. The non-transitory storage element can be accessed by a general purpose or special purpose computer, including the functional design of any special purpose processor. Few examples of such non-transitory storage element can include RAM, ROM, EEPROM, CD-ROM or other optical disk storage or other magnetic. The processor and non-transitory storage element (or memory) are known in the art, thus, any additional functional or structural details are not required for the purpose of the current disclosure.

The invention claimed is:
1. A method for constructing a 3-D avatar, said method comprising:
   capturing one or more frames of a head by a frame capture unit in a first position of a user;
   capturing one or more frames of the body by the frame capture unit in a second position of a user;
   selecting frames from the one or more frames of the head and estimating frame-to-frame pixel correspondences among selected frames of the head and creating a 3-D mesh of the head;
   selecting frames from the one or more frames of the body and estimating frame-to-frame pixel correspondences among selected frames of the body and creating a 3-D mesh of the body;
   aligning the 3-D mesh of the body with the 3-D mesh of the head; and
   constructing a resolved 3-D avatar of the user by applying texture to the aligned 3-D mesh by projecting colors frames to the mesh posed in each frame pose.

2. The method of claim 1, comprising: referencing a training dataset to predict a high quality (HQ) depth sensor image frame reprojection from a capturing view of a low quality (LQ) depth sensor.

3. The method of claim 2, wherein the referencing of the training dataset is for constructing the resolved 3-D avatar of the user.

4. The method of claim 1, wherein the resolved 3-D avatar of the user is constructed from frames captured from a user mobile device.

5. The method of claim 1, comprising: performing depth-based segmentation to subtract background for each of the selected body frames and each of the selected head frames.

6. The method of claim 1, comprising the step of aligning a depth and color stream for each of the selected body and head frames.

7. The method of claim 1, comprising the step of predicting correspondences between image pixels from each of the body and head frames with a point on a surface of a parametric body model.

8. The method of claim 1, comprising the step of providing guidance on at least one of location mark, pose, or actions for an ideal frame capture via a visual-based and/or vocal-based interface.

9. The method of claim 1, wherein the resolved 3-D avatar is incorporated into an on-site and/or on-line clothing retail experience.

10. The method of claim 9, wherein the clothing retail experience comprises at least one of providing body dimensions or a virtual garment fitting.

11. The method of claim 1, wherein the resolved 3-D avatar is incorporated into an on-site and/or on-line Augmented Reality/Virtual Reality (AR/VR) experience.

12. The method of claim 1, wherein the resolved 3-D avatar is incorporated into an on-site and/or on-line gaming experience.

13. The method of claim 1, wherein the resolved 3-D avatar is incorporated into an on-site and/or on-line telemedical application.

14. The method of claim 1, wherein the resolved 3-D avatar is incorporated into an on-site and/or on-line dermatological or cosmetic purpose.

15. The method of claim 1, wherein the resolved 3-D avatar is incorporated for surveillance, security, identification, or verification purposes.

16. The method of claim 15, wherein the captured frames are from a remote camera and/or database.

17. The method of claim 1, comprising: implementing on a host by at least one of an SDK, API, or web browser.

18. A method for constructing a three dimensional (3-D) avatar comprising:
selecting two or more frames from a plurality of captured video frames of a human body of a user by a capturing device;
selecting two or more frames from a plurality of captured video frames of a human head of the user by a capturing device;
performing depth-based segmentation to subtract background for each of the selected two or more body frames and the two or more selected head frames;
aligning a depth and color stream for each of the two or more selected body frames and the two or more selected head frames;
predicting correspondences between image pixels from each of the two or more selected body and the two or more selected head frames and point on a surface of a parametric body model;
estimating frame-to-frame correspondences for creating a 3-D mesh for the body and estimating frame-to-frame correspondences for creating a 3-D mesh for the head;
aligning the head 3-D mesh with the body 3-D mesh; and
constructing a three-dimensional avatar of the user by applying texture to the aligned 3-D mesh by projecting two or more colors frames to the mesh posed in each frame pose.

19. A system for constructing a resolved 3-D avatar, said system comprising:
a memory element operably coupled to a processor;
a program executable by the processor to:
select from captured video frames of a human body two or more frames and select from captured video frames of head of a user two or more frames, wherein the separately captured video frames are captured by a same video capturing device;
estimate frame-to-frame pixel correspondences among selected two or more frames of the body for creating a 3-D mesh of the body;
estimate frame-to-frame pixel correspondences among selected two or more frames of the head for creating a 3-D mesh of the head;
align the 3-D mesh of the body with the 3-D mesh of the head;
construct a resolved 3-D avatar of the user by applying texture to the aligned 3-D mesh; and
projecting the colors frames to the mesh posed in each frame pose.

20. A system for constructing a resolved 3-D avatar, said system comprising:
a memory element operably coupled to a processor;
a program executable by the processor to:
select separately captured video frames of a human body and head of a user;
perform depth-based segmentation to subtract background for each of the selected body and head frames, wherein the separately captured video frames are captured by a same video capturing device;
align a depth and color stream for each of the selected body and head frames;
predict correspondences between image pixels from each of the body and head frames and point on a surface of a parametric body model;
estimate frame-to-frame correspondences for creating a 3-D mesh for each of the body and the head;
align the head 3-D mesh with the body 3-D mesh; and
construct a three-dimensional avatar of the user by applying texture to the 3-D mesh by projecting the colors frames to the mesh posed in each frame pose.

21. A system for constructing a resolved 3-D avatar, said system comprising:
a memory element operably coupled to a processor;
a program executable by the processor to:
perform a depth-based segmentation to subtract background for each of a selected body and head frames by a segmentation unit within a pre-processing module, wherein the selected body and head frames are captured by a same video capturing device;
align a depth and color stream for each of the selected body and head frames for creating a first 3-D mesh of the body and a second 3-D mesh of the head by a mesh unit within a processing module;
align the second 3-D mesh of the head 3-D mesh with the first 3-D mesh of the body by an alignment unit within the processing module; and construct a three-dimensional avatar of the user by applying texture to the aligned 3-D mesh by projecting the colors frames to the mesh posed in each frame pose by a texturing unit within a post-processing module.

* * * * *